(12) United States Patent
Lee et al.

(10) Patent No.: US 7,160,869 B2
(45) Date of Patent: Jan. 9, 2007

(54) BIOLOGICALLY ACTIVE METAL-CONTAINING NUCLEIC ACIDS

(75) Inventors: Jeremy S. Lee, Saskatoon (CA); Palok Aich, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 298 days.

(21) Appl. No.: 10/061,979

(22) Filed: Jan. 31, 2002

(65) Prior Publication Data

US 2003/0013672 A1 Jan. 16, 2003

Related U.S. Application Data

(63) Continuation-in-part of application No. 09/213,052, filed on Dec. 16, 1998, now Pat. No. 6,432,641.

(60) Provisional application No. 60/292,881, filed on May 24, 2001.

(51) Int. Cl.
*A61K 37/70* (2006.01)
*A61K 39/00* (2006.01)
*A01N 43/04* (2006.01)
*C12P 29/00* (2006.01)
*C12N 15/00* (2006.01)
*C12N 15/86* (2006.01)
*C07K 16/00* (2006.01)

(52) U.S. Cl. ............... 514/44; 435/69.1; 435/320.1; 435/455; 530/387.9; 424/184.1

(58) Field of Classification Search .......... 514/44; 435/69.1, 320.1; 424/184.1; 530/387.9; 536/25.4, 22.1
See application file for complete search history.

(56) References Cited

U.S. PATENT DOCUMENTS

| | | |
|---|---|---|
| 4,562,157 A | 12/1985 | Lowe et al. |
| 5,278,043 A | 1/1994 | Bannwarth et al. |
| 5,532,129 A | 7/1996 | Heller |
| 5,556,752 A | 9/1996 | Lockhart et al. |
| 5,561,071 A | 10/1996 | Hollenberg et al. |
| 5,589,692 A | 12/1996 | Reed |
| 5,591,578 A | 1/1997 | Meade et al. |
| 5,679,647 A | 10/1997 | Carson et al. |
| 5,705,348 A | 1/1998 | Meade et al. |
| 5,770,369 A | 6/1998 | Meade et al. |
| 5,780,234 A | 7/1998 | Meade et al. |
| 5,780,448 A | 7/1998 | Davis |
| 5,824,473 A | 10/1998 | Meade et al. |
| 5,830,877 A | 11/1998 | Carson et al. |

FOREIGN PATENT DOCUMENTS

| | | |
|---|---|---|
| WO | WO 95/15971 | 6/1995 |
| WO | WO 96/40712 | 12/1996 |
| WO | WO 97/46568 | 12/1997 |
| WO | WO 99/31115 | 6/1999 |

OTHER PUBLICATIONS

Rekvig, O.P. The immunological basis for selecting anti-dsDNA antibody assays, Internet publication.*
Falo and Storkus, Giving DNA vaccines a helping hand, Nov. 1998, vol. 4(11) p. 1239-1240.*
Meng R.D. and El-Deiry, W.S. Tumor Suppressor Genes as Targets for Cancer Gene Therapy, 1999, Gene Therapy of Cancer, Chapter 1 pp. 3-18.*
Aidsmap, DNA vaccines and replicons, internet document downloaded Aug. 19, 2005.*
Bandekar et al., "Copper (II) Nucleic Acid Interactions—a Conformational Study," *Chemical Abstracts*, 91(23):190 abstract # 188121w (XP-002100894) (Dec. 3, 1979).
Maskos et al., "Interaction of Metal Ions with Nucleic Acids. Interaction of Copper (II) with Pyrimidine Nucleosides and Their Derivatives," *Chemical Abstracts*, 92(7):218 abstract # 53563s (XP-002100895) (Feb. 18, 1980).
Nielsen et al., "Sequence-Selective Recognition of DNA by Strand Displacement with a Thymine-Substituted Polyamide," *Science*, 254:1497-1500 (Dec. 6, 1991).
Braun et al., "DNA-Templated Assembly and Electrode Attachment of a Conducting Silver Wire," *Nature*, 391:775-778 (Feb. 19, 1998).
Aich et al., "M-DNA: A Complex Between Divalent Metal Ions and DNA Which Behaves as a Molecular Wire," *Journal of Molecular Biology*, 294:477-485 (1999).
Wang et al., "Electrochemically Induced Release of DNA from Gold Ultramicroelectrodes," *Langmuir*, 15:6541-6545 (1999).
Porath et al., "Direct Measurement of Electrical Transport Through DNA Molecules," *Nature*, 403:635-638 (Feb. 10, 2000).
Gelbart et al., "DNA-Inspired Electrostatics," *Physics Today*, 53:38-44 (Sep. 2000).
Ratkin et al., "Metallic Conduction Through Engineered DNA: DNA Nanoelectronic Building Blocks," *Physical Review Letters*, 86: 3670-3673 (Apr. 16, 2001).
US 5,804,556, 09/1998, Carson et al. (withdrawn)

\* cited by examiner

*Primary Examiner*—Dave Trong Nguyen
*Assistant Examiner*—Maria Marvich
(74) *Attorney, Agent, or Firm*—Townsend and Townsend and Crew LLP (57) ABSTRACT

The invention relates to polymers comprising metal-containing nucleic acid duplexes. Methods of using the metal-containing nucleic acid duplexes to provoke physiological responses in a host animal are provided, such as immunological methods that produce antibodies in the host.

15 Claims, 7 Drawing Sheets

BIOLOGICALLY ACTIVE METAL-CONTAINING NUCLEIC ACIDS

CROSS-REFERENCE TO RELATED APPLICATIONS

This application is a continuation-in-part of application Ser. No. 09/213,052 filed 16 Dec. 1998, now U.S. Pat. No. 6,432,641, incorporated herein by reference. This application is also a continuation-in-part of co-pending Application Ser. No. 60/292,881 filed 24 May 2001, incorporated herein by reference.

FIELD OF THE INVENTION

The invention is in the field of nucleic acid biochemistry, particularly methods for using robust metal-containing nucleic acids to elicit physiological responses.

BACKGROUND OF THE INVENTION

Polymeric molecular conductors are known. For example, some naturally occurring proteins facilitate electron transfer in such fundamental biological processes as photosynthesis and respiration. Electron transfer in such systems is generally understood to occur as the result of quantum mechanical 'tunnelling' of electrons along pathways, molecular orbitals, that connect one atom to the next in the polymer.

It has been proposed that the stacked aromatic bases of DNA may act as a 'π-way' for the transfer of electrons (Dandliker et al., 1997; Hall et al., 1996; Arkin et al., 1996). This proposal is based on a theory that the stacked arrangement of bases on complementary strands juxtaposes the shared electrons in the π orbitals of the aromatic nitrogen bases, facilitating quantum mechanical tunnelling along the stack of base pairs. A number of experiments have supported the view that this effect exists, while other experiments have provided contrary evidence that the effect is limited or non-existent.

For example, experiments have been reported to demonstrate that photoinduced electron transfer may occur between two metallointercalators tethered at either end of a 15-base pair DNA duplex (Murphy et al., 1993). On the other hand, kinetic analysis of distance-dependent electron transfer in a DNA hairpin has been used to show that DNA is a poor conductor, only somewhat more effective than proteins as a conductor of electrons (Lewis et al., 1997; Taubes 1997).

U.S. Pat. Nos. 5,591,578; 5,705,348; 5,770,369; 5,780,234 and 5,824,473 issued to Meade et al. on, respectively, 7 Jan. 1997, 6 Jan. 1998, 23 June 1998, 14 Jul. 1998 and 20 Oct. 1998 (and incorporated herein by reference) disclose nucleic acids that are covalently modified with electron transfer moieties along the nucleic acid backbone. Meade et al. teach that such modifications are necessary for nucleic acids to efficiently mediate electron transfer.

The theory of π-orbital-mediated conductance along a nucleic acid duplex suggests that, as a precondition, such conductance requires a stable duplex with stacked base pairs. The effect on duplex stability of the binding of metal ions to nucleic acids, particularly DNA, has been studied extensively for nearly 40 years. In general, cations that bind primarily to the phosphate backbone will stabilize the duplex conformation, whereas those that bind to the bases will tend to denature the duplex. These effects are readily demonstrated with thermal denaturation profiles (Tm measurements). Experiments of this sort show that most monovalent cations, such as $Na^+$, which tend to interact with the phosphate backbone, stabilize the duplex. This effect is reflected in the finding that there is approximately a 12° C. increase in Tm for each 10-fold increase in monovalent cation concentration (Marmur and Doty 1962). An exception to this general principle is $Ag^+$, which binds tightly to nitrogen bases, destabilizes the duplex, and therefore decreases the duplex Tm (Guay and Beauchamp 1979). Similarly, multivalent ions, particularly polyamines, which interact with the phosphate backbone are very effective duplex stabilizers.

For divalent metal cations, a series can be written in increasing order of DNA destabilization: $Mg^{2+}$, $Co^{2+}$, $Ni^{2+}$, $Mn^{2+}$, $Zn^{2+}$, $Cd^{2+}$, $Cu^{2+}$ (Eichorn 1962; Eichorn and Shin 1968). At one end of the spectrum, $Mg^{2+}$ increases the Tm at all concentrations; at the other end of the spectrum, sufficiently high concentrations of $Cu^{2+}$ will lead to complete denaturation of the duplex at room temperature (Eichorn and Shin 1968). This series also correlates with the ability of the divalent cations to bind to the bases (Hodgson 1977; Swaminathan and Sundaralingham 1979).

Cations are also involved in promoting several other structural transitions and dismutations in nucleic acids. It has previously been reported that $Zn^{2+}$ and some other divalent metal ions bind to duplex DNA at pHs above 8 and cause a conformational change (Lee et al., 1993). Preliminary characterization of the resulting structure incorporating zinc showed that it retained two antiparallel strands but that it was distinct from normal 'B' DNA: it did not bind ethidium bromide, it appeared to lose the imino protons of both A-T and G-C base pairs upon addition of a stoichiometric amount of $Zn^{2+}$, and it contained at least 5% fewer base pairs per turn than 'B' DNA.

SUMMARY OF THE INVENTION

In one aspect, the invention provides methods of producing a physiological response in an animal, such as a human, comprising administering to the animal a metal-containing nucleic acid duplex. It has surprisingly been discovered that exemplified embodiments of the metal-containing nucleic acids of the invention are nuclease resistant, which may facilitate the production of a physiological response in a host, such as an immune response. In some embodiments, the physiological response may involve expression of the metal-containing nucleic acid, for example to produce antigenic proteins or to inhibit expression of a complementary gene, for example by an antisense mechanism.

The metal-containing nucleic acid duplex may comprise a first strand of nucleic acid and a second strand of nucleic acid, the first and the second nucleic acid strands each comprising a plurality of nitrogen-containing aromatic bases covalently linked by a backbone. The nitrogen-containing aromatic bases of the first nucleic acid strand may be joined by hydrogen bonding to the nitrogen-containing aromatic bases of the second nucleic acid strand. The nitrogen-containing aromatic bases on the first and the second nucleic acid strands may form hydrogen-bonded base pairs in stacked arrangement along the length of the metal-containing nucleic acid duplex. At least some of the hydrogen-bonded base pairs may comprise an interchelated divalent metal cation coordinated to a nitrogen atom in one of the aromatic nitrogen-containing aromatic bases.

In another aspect, the invention provides an electrical conductor comprising an electron source electrically coupled to a metal-containing nucleic acid duplex, to form a conductive metal-containing nucleic acid duplex (CM- CNA). An electron sink may also be electrically coupled to the metal-containing nucleic acid duplex. In some embodiments, the conductive metal-containing nucleic acid comprises a first strand of nucleic acid and a second strand of nucleic acid. The first and the second nucleic acid strands include a plurality of nitrogen-containing aromatic bases covalently linked by a backbone (the backbone may be made up of phosphodiester bonds, as in DNA or RNA, or alternative structures as discussed below). The nitrogen-containing aromatic bases of the first nucleic acid strand are joined by hydrogen bonding to the nitrogen-containing aromatic bases of the second nucleic acid strand. The nitrogen-containing bases on the first and the second nucleic acid strands form hydrogen-bonded base pairs in stacked arrangement along the length of the conductive metal-containing nucleic acid. At least some, and preferably each, of the hydrogen-bonded base pairs comprises an interchelated divalent metal cation coordinated to a nitrogen atom in one of the aromatic nitrogen-containing bases.

The electron source electrically coupled to the conductive metal-containing nucleic acid may be an electron donor molecule capable of donating an electron to the conductive metal-containing nucleic acid duplex. Similarly, the electron sink may be an electron acceptor molecule capable of accepting an electron from the conductive metal-containing nucleic acid. The electron donor molecule may be a fluorescent molecule, such as fluorescein. Similarly, the electron acceptor molecule may be a fluorescent molecule, such as rhodamine. It will be appreciated that some molecules may act both as electron donors and electron acceptors in various embodiments of the invention.

The metal-containing nucleic acid may be made of deoxyribonucleic acid strands, which together produce metal-containing DNA (M-DNA). The nitrogen-containing aromatic bases in the nucleic acid may be the naturally occurring bases: adenine, thymine, guanine and cytosine.

In various embodiments, divalent metal cations used to make metal-containing nucleic acids, and conductive metal-containing nucleic acids may for example be $Zn^{2+}$, $Co^{2+}$, or $Ni^{2+}$. Under some conditions, selected divalent metal cations may not produce a conductive metal-containing nucleic acid duplex, and the present invention provides simple assays to determine whether a particular divalent metal cation will work to produce conductive metal-containing nucleic acid.

In some embodiments, metal cations, such as divalent metal cations, may be substituted for the imine protons of aromatic nitrogen-containing bases in the metal-containing nucleic acids of the invention. In some embodiments, for example, divalent metal cations may be substituted for the N3 imine proton of thymine, or the imine protons of the N1 nitrogen atom of guanine.

The invention provides a method for making metal-containing nucleic acid duplexes, including conductive metal-containing duplexes. A nucleic acid duplex is subjected to basic conditions in the presence of a divalent metal cation under conditions effective to form a conductive metal-containing nucleic acid duplex. Electron sources and sinks may be electrically coupled to the conductive metal-containing nucleic acid duplex, which may take the form of various embodiments discussed above.

The invention provides methods for detecting the formation of conductive metal-containing nucleic acid duplexes from first and second nucleic acid strands. The nucleic acid strands are mixed under conditions which allow complementary stands to hybridize and subjected to basic conditions in the presence of a divalent metal cation under conditions effective to form a conductive metal-containing nucleic acid duplex if the first and second strands are complementary. An electron source is provided electrically coupled to the conductive metal-containing nucleic acid duplex. Conductance of electrons between the electron source and the conductive metal-containing nucleic acid duplex is then tested to determine whether a conductive metal-containing nucleic acid duplex has formed. The conductive metal-containing nucleic acid duplex may take the form of various embodiments discussed above.

Metal-containing nucleic acid duplexes of the invention may be used to carry electrons. They may also be used to raise antibodies in an animal, producing antibodies to metal-containing nucleic acid duplexes or proteins encoded by nucleic acids of the invention. In some embodiments, this latter use takes advantage of the finding that in some embodiments and under certain conditions metal-containing nucleic acid duplexes may be nuclease resistant.

BRIEF DESCRIPTION OF THE DRAWINGS

FIG. 1 shows the release of protons on formation of M-DNA. Upon addition of $NiCl_2$, protons are released and KOH was added (left axis) to maintain the pH at 8.5. After each addition 10 μl was removed to assess the formation of M-DNA by the ethidium fluorescence assay (Lee et al, 1993) (right axis). The experiment was performed in a 10 mL volume, with 1.1 mM in base pairs of calf thymus DNA. The DNA was dialyzed against water and sheared by passing through a 30 gauge needle five times. Arrow (a) indicates the putative point at which M-DNA formation began. This lag phase is proportional to the DNA concentration (data not shown) and may be due to the initial binding of the metal ion to the outside of the helix. Arrow (b) indicates the point at which 1.1 mM of $H^+$ had been released, beyond which precipitation of the M-DNA was observed.

FIG. 4 shows the nuclease resistance of M-DNA. The amount of duplex DNA remaining as a function of time was assessed by the ethidium fluorescence assay (under conditions where M-DNA rapidly reverts to B-DNA, pH 8, 0.1 mM EDTA, so that ethidium can bind the DNA). The digestion was performed at 37° C. in 10 mM Tris-HCl, pH 7.4, 5 mM $MgCl_2$, 1 mM $NiCl_2$, 1 mg/ml gelatin, and 0.2 μg/ml DNase I. The $Ni^{2+}$ form of M-DNA was preformed for the assay at pH 9 before adding it to the digestion buffer; B-DNA was added directly to the digestion buffer. The graph shows that the M-DNA is resistant to nuclease digestion while B-DNA is digested in about 10 minutes. The results also demonstrate that the $Ni^{2+}$ form of M-DNA is stable at physiological pH, a characteristic which facilitates the use of $Ni^{2+}$-M-DNA to mediate physiological responses in vivo, such as DNA immunization (in which the DNA 'vaccine' expresses an antigenic protein) or antisense applications (in which injected M-DNA inhibits the expression of a complementary gene).

FIG. 5 shows that M-DNA is immunogenic. Balb/C mice were immunized interperitoneally three times at ten day intervals with 10 μg of nickel-containing M-DNA, with and without methylated bovine serum albumin (Me-BSA). The first injection was with complete Freunds adjuvant and subsequent injections were with incomplete Freunds adjuvant. Three days after the final injection, blood was obtained by tail bleeding and the serum was tested for the present of antiM-DNA antibodies using nickel M-DNA coated polyvinylchloride plates in a SPIRA assay, using methods known in the art (Braun and Lee, 1988).

DETAILED DESCRIPTION OF THE INVENTION

In one aspect, the invention provides a conductive metal-containing nucleic acid duplex comprising an electron source electrically coupled to a nucleic acid duplex in which at least some of the stacked, aromatic nitrogen-containing base pairs chelate divalent metal cations. In such an embodiment, the metal-containing nucleic acid duplex acts as an electron acceptor, receiving electrons from the electron donor. In one embodiment of this aspect of the invention, the imine protons of a DNA duplex may be replaced by $Zn^{2+}$, $Co^{2+}$ or $Ni^{2+}$. The metal-containing DNA duplex may, for example be electronically coupled to molecular electron donors or electron sinks, such as fluorescein or rhodamine respectively, by covalent attachment.

In alternative embodiments, metal cations for incorporation into a metal-substituted duplex of the invention may be selected from the group consisting of the cations of Li, Be, Na, Mg, Al, K, Ca, Sc, Ti, V, Cr, Mn, Fe, Co, Ni, Cu, Zn, Ga, Ge, As, Rb, Sr, Y, Zr, Nb, Mo, Tc, Ru, Rh, Pd, Ag, Cd, In, Sn, Sb, Cs, Ba, La, Ce, Pr, Nd, Pm, Sm, Eu, Gd, Tb, Dy, Ho, Er, Tm, Yb, Lu, Hf, Ta, W, Re, Os, Ir, Pt, Au, Hg, Tl, Pb, Bi, Po, Fr, Ra, Ac, Th, Pa, U, Np and Pu. For example, in some embodiments varying amounts of metal cations may be incorporated into a duplex, such as $Zn^{2+}$, $Ni^{2+}$, $Co^{2+}$, $Cd^{2+}$, $Hg^{2+}$, $Pt^{2+}$ and $Ag^{1+}$, where metal ions such as $Cd^{2+}$, $Hg^{2+}$, $Pt^{2+}$ and $Ag^{1+}$ may constitute only a portion of the metal ions in the duplex, in effect 'doping' the duplex. The formation of a metal-substituted duplex using alternative cations under alternative conditions may be monitored, for example, using an ethidium bromide fluorescence assay as described herein.

In one aspect, the present invention provides a method for converting a nucleic acid duplex to M-DNA or conductive metal-containing nucleic acid. A nucleic acid duplex is treated with sufficient base in the presence of an adequate concentration of an appropriate divalent metal ion to result in the chelation of the divalent metal ion by the aromatic nitrogen bases of the nucleic acid. Such treatment is carried out for a sufficient period of time to produce a modified duplex comprising the divalent metal cation coordinated to nitrogen atoms in the aromatic nitrogen-containing bases of base pairs.

In one embodiment, conditions for converting DNA, such as a B-DNA, to M-DNA comprise subjecting the DNA to a solution at pH 8.5 or greater, with approximate concentrations of divalent metal ions as follows: 0.1 mM $Zn^{2+}$ or 0.2 mM $Co^{2+}$ or 0.2 mM $Ni^{2+}$. The conditions necessary to form M-DNA will vary depending on the metal ion or ions used and the nature of the nucleic acid. Those skilled in this art will appreciate that routine experiments may be carried out to determine appropriate conditions, varying parameters such as pH, nucleic acid concentration, metal ion concentration and the ratio of the metal ion concentration to the nucleic acid concentration. In some embodiments, a pH equal to or greater than 8, or greater than 8.5, may be required, and a suitable nucleic acid to metal ion ratio may be about 1:1.5 to about 1:2.0.

The conductive metal-containing nucleic acid may be electrically coupled to an electron source and an electron sink. For example, molecular electron donors and acceptors may act respectively as electron sources and electron sinks. In alternative embodiments, the electron donors and acceptors may be in solution, interacting transiently with the conductive metal-containing nucleic acid, or they may be in the form of a solid support, such as an electrode.

Solid phase supports to which the conductive metal-containing nucleic acid is attached may serve as electron sources, sinks or both. For example, immobilized arrays of conductive metal-containing nucleic acid may be prepared in accordance with the teaching of U.S. Pat. No. 5,556,752, issued 17 Sep. 1996 to Lockhart et al. (the "'752 Patent", incorporated herein by reference). Such immobilized arrays may then be used, as described therein and modified as necessary, to detect hybridization. In accordance with the present invention, the step of hybridizing the target nucleic acid to the immobilized probe may be followed, or accompanied, by the step of converting resulting duplexes to conductive metal-containing nucleic acid duplexes under basic conditions in the presence of a divalent metal cation, as described herein. Electron donors and acceptors may be provided in such a system, as described in the '752 Patent, so that the conductivity of the resulting conductive metal-containing nucleic acid duplex is detectable at the surface of the immobilization substrate, as is also described in the '752 Patent. It will be appreciated that such a system involves the use of a conductive metal-containing nucleic acid duplex as a conductor, which is one aspect of the present invention.

The formation of conductive metal-containing nucleic acid may be used to assay a variety of nucleic acid interactions. For example, the amplification of a target sequence using the polymerase chain reaction (PCR) may be assayed using methods of the present invention. In one aspect of such an assay, one PCR primer is provided with an electron donor moiety and the other PCR primer is provided with an electron acceptor moiety. In accordance with this aspect of the present invention, following PCR amplification cycles, the reaction mixture may be subjected to basic conditions in the presence of a divalent metal cation to promote the formation of conductive metal-containing nucleic acid. If the PCR amplification has been successful, conductive metal-containing nucleic acid will have formed and will be detectable as disclosed herein as a result of characteristic conductance between the electron donor and the electron acceptor. Unsuccessful amplification will leave the electron transfer moieties on the primers electrically uncoupled. In some embodiments, this approach may have the advantage of allowing detection of amplification without the need to separate the PCR primers from the PCR reaction mixture following amplification cycles. In accordance with this aspect of the invention, a kit may be provided comprising PCR primers having electron donors and electron acceptors, together with instructions for subjecting an amplification reaction mixture to basic conditions in the presence of a divalent metal cation to form conductive metal-containing nucleic acid. Such kits with appropriate instructions may also be provided for the other aspects of the invention disclosed herein Ligation of nucleic acids may also be assayed using methods of the present invention, wherein successful ligation is detectable by the formation of conductive metal-containing nucleic acid. In such a system, one of the nucleic acid duplexes to be ligated may be provided with an electron donor moiety, while the other nucleic acid duplex to be ligated is provided with an electron acceptor moiety. Ligation and subsequent formation of a conductive metal-containing nucleic acid electrically couples the electron transfer moieties, producing a signal under appropriate conditions that is indicative of successful ligation. A kit may be provided for such a reaction, comprising an electron donor label and an electron acceptor label, together with instructions for coupling the electron donor and electron acceptor to nucleic acids that are to be ligated, and subjecting the ligation reaction mixture to basic conditions in the presence of a divalent metal cation to form conductive metal-containing nucleic acid.

In one embodiment of the invention, conditions are adapted to convert a B-DNA duplex to M-DNA. In one aspect of the invention, M-DNA is formed at pHs at or above 8 in the presence of sufficient amounts (preferably, in some embodiments, about 0.1 mM, provided the nucleic acid concentration is less than about 0.1 mM) of $Zn^{2+}$, $Ni^{2+}$ or $Co^{2+}$. In such an embodiment, $Mg^{2+}$ or $Ca^{2+}$ may not serve to produce M-DNA (Lee et al., 1993). A wide variety of bacterial and synthetic DNAs may dismutate to M-DNA under these conditions. In some embodiments, the process of M-DNA formation may be reversible by lowering the pH and/or addition of EDTA. In some embodiments, Ni-M-DNA requires EDTA to be converted to 'B' DNA at pHs greater than about 7. In some embodiments, poly[d(AT)] may not be convertible to M-DNA under such conditions. Unlike B-DNA, ethidium will not bind to some embodiments of M-DNA, and this property forms the basis of a rapid and sensitive "ethidium fluorescence assay" that may be used to monitor M-DNA formation (Lee et al., 1993).

M-DNA may be readily interconverted with B-DNA; therefore, useful techniques for manipulation of DNA such as cutting and splicing, and for the self-assembly of a variety of structures (such as two and three-way junctions) may be used with M-DNA forming sequences, as are well known in the art (Lilley and Clegg, 1993; Seeman and Kallenbach, 1994). In addition, the binding of sequence-specific proteins to conductive metal-containing nucleic acids may be manipulated in some embodiments to interfere with conductance of the M-DNA so as to mimic electric switches and resistors.

Figure 6:
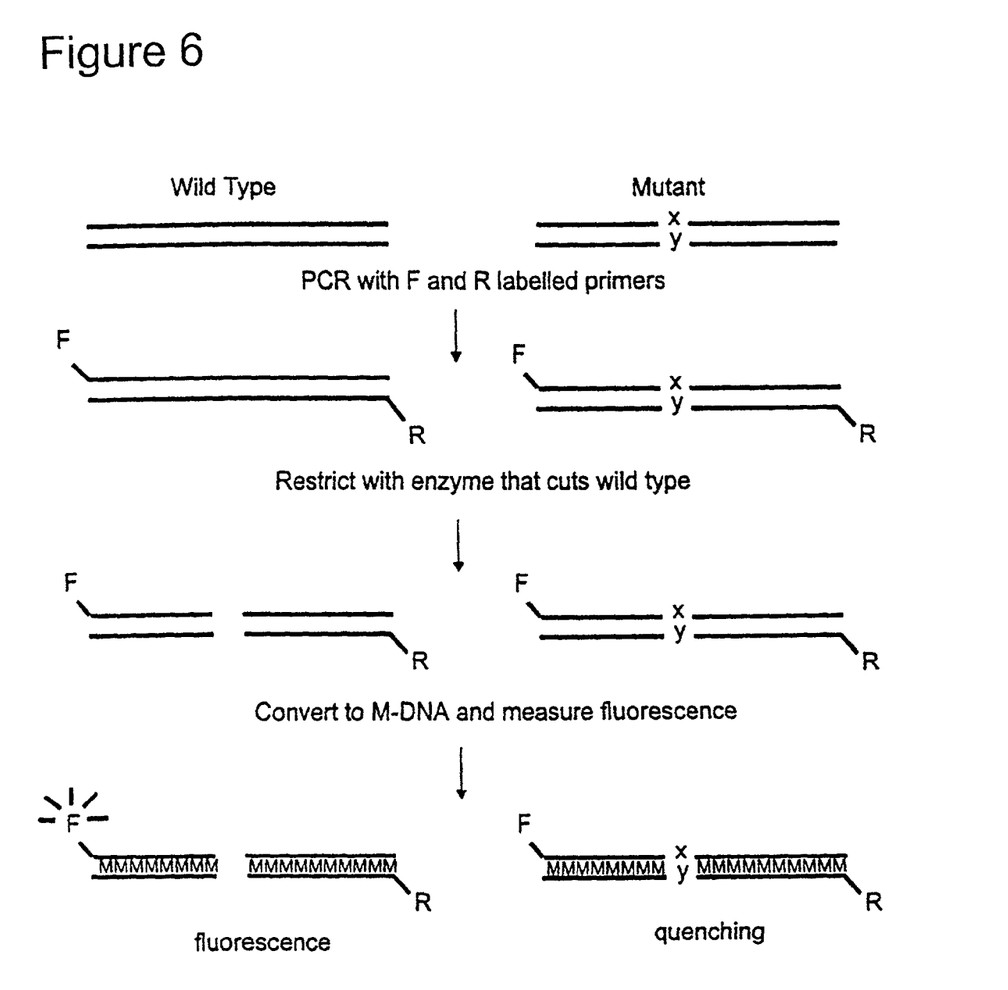
FIG. 6 is a schematic illustration showing as aspect of the invention that comprises a method of sequence analysis, in which one sequence that is susceptible to cutting by a restriction endonuclease may be distinguished from another sequence that is not susceptible on the basis of the presence or absence of conductance in an M-DNA duplex formed between an electron donor, shown as "F"0 for fluorescein in the figure, and an electron acceptor, shown as "R" for rhodamine in the figure.

One aspect of the invention provides methods for detecting particular sequences in genomic analysis, such as methods for detecting particular mutations. In one such aspect of the invention, as shown in FIG. 6, the nucleic acid to be analysed (shown as wild type or mutant) is amplified by PCR using primers, one of the primers being labelled with an electron donor and the other being labeled with an electron acceptor, such as fluorescein (shown as "F") and rhodamine (shown as "R") respectively. Following amplification, the nucleic acid is treated with a restriction enzyme which may or may not cut the amplified sequence, depending upon the nature of the amplified sequence. For example, the restriction enzyme may only cut one allele of a gene, leaving other alleles or non-wild type sequences uncleaved (as shown in FIG. 6, where X and Y represent a mutant base pair). Following treatment with the restriction enzyme the amplified sequence may be subjected to conditions suitable for the formation of a conductive metal-containing nucleic acid, for example amplified DNA duplexes may be converted to M-DNA. The fluorescence of the sample may then be measured. If the amplified duplex spans the region between the primers, as in the mutant gene of FIG. 6, then the fluorescence of the amplified nucleic acid will be quenched by electron transfer along the conductive metal-containing nucleic acid. If, on the other hand, as in the wild type gene of FIG. 6, the amplified duplex has been cut by the restriction enzyme, the fluorescence of the electron donor will not be quenched. A sample in which half of the sequences formed conductive metal-containing nucleic acid and half did not, such as may be the case in an analysis of a sample from an individual with an autosomal recessive mutation, the degree of fluorescence may be intermediate. Sequence analysis in accordance with this aspect of the invention may be carried out in an automated fashion. For example, in one aspect this approach may simultaneously use multiple reaction wells to carry out such reactions, each well containing different reagents, such as different primers or different restriction enzymes, to yield an abundance of information about a particular sample in a relatively short time without the necessity of electrophoresis or other more time-consuming steps.

Figure 7:
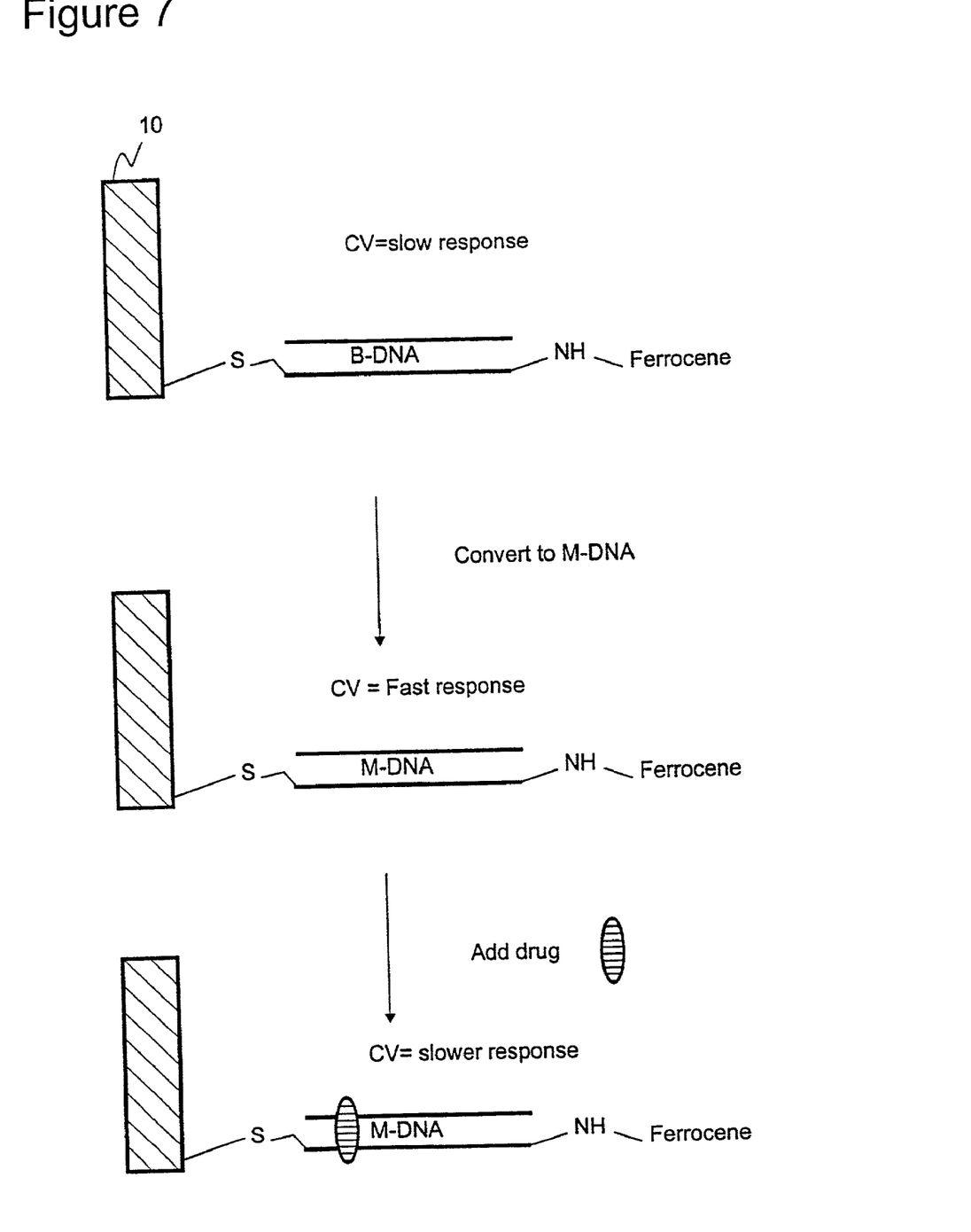
FIG. 7 is a schematic illustration showing a nucleic acid coupled to electrode 10 and subjected to conditions suitable to form M-DNA, while measurements are taken of the conductance of the conductive metal-containing nucleic acid by cyclic voltammetry, both in the absence and presence of a DNA-binding drug.

In an alternative aspect, the invention provides a sensor for monitoring the presence of nucleic acid binding moieties in a sample. In one embodiment of this aspect of the invention, as shown in FIG. 7, a nucleic acid duplex capable of forming a conductive metal-containing nucleic acid is attached between an electron sink and an electron donor, such as ferrocene, the nucleic acid is exposed to a sample under conditions that favour the formation of a conductive metal-containing nucleic acid duplex, the binding of a moiety to the nucleic acid is detected by a change in the conductance of the nucleic acid. For example, DNA binding molecules may convert M-DNA back to B-DNA under such conditions, and thereby prevent or reduce the conductive metal-containing nucleic acid mediated quenching of a fluorescent electron donor that is coupled to the nucleic acid. In one embodiment, the nucleic acid may be coupled to an electrode (for example as described in Braun et al., Nature, 391:775–778, 1998, incorporated herein by reference), such as gold electrode 10 of FIG. 7, and the electrode may then be used to measure the conductance of the conductive metal-containing nucleic acid while the electrode is exposed to a sample. In some embodiments, for example, such conductance measurements may utilize cyclic voltammetry (shown as CV in FIG. 7). Such, assays involving the detection of variations in the conductance of a conductive metal-containing nucleic acid may be used in various embodiments of the invention to detect interactions between nucleic acids and a wide variety of other moieties, such as small molecules, triplex-forming oligonucleotides and DNA-binding proteins.

In some embodiments, the conductance of conductive metal-containing nucleic acid duplexes may be enhanced by modification of the nucleic acid with electron transfer moieties, such as is taught in the following U.S. Pat. Nos. 5,591,578; 5,705,348; 5,770,369; 5,780,234 and 5,824,473 issued to Meade et al. on respectively 7 Jan. 1997, 6 Jan. 1998, 23 Jun. 1998, 14 Jul. 1998 and 20 Oct. 1998 (and incorporated herein by reference).

In the context of the present invention, 'conductive' means capable of conducting electrons. An electron source in accordance with the present invention may be any compound or substance capable of providing electrons, such as an atomic or molecular conductor. Similarly, an electron sink (or acceptor) may be any compound or composition capable of accepting electrons. A nucleic acid duplex comprises hybridized strands of nucleic acid molecules. A strand of nucleic acid comprises at least two nucleotides covalently linked by a backbone. The backbone may be made up of polymeric phosphodiester bonds, as in DNA or RNA. Alternatively, other backbone structures may be effective to appropriately align the aromatic nitrogen-containing bases in a stacked arrangement capable of chelating metal ions and conducting electrons. For example, phosphoramide, phosphorothioate, phosphorodithioate, O-methylphosphoroamidite or peptide nucleic acid linkages may be effective to form such a backbone. Similarly, other components of the backbone may vary in accordance with the invention, encompassing deoxyribose moieties, ribose moieties, or combinations thereof. If RNA is used, those skilled in this art will appreciate that conditions must be adapted to account for the fact that RNA is labile in basic solution, so that conversion of RNA to conductive metal-containing nucleic acid may require modified reaction conditions which avoid hydrolysis of the RNA. In one aspect of the invention, the nitrogen-containing aromatic bases are preferably those that occur in native DNA and RNA: adenine, thymine, cytosine guanine or uracil. However, those skilled in this art will understand that alternative nitrogen-containing aromatic bases may be utilized, preferably they are capable of interchelating a divalent metal ion, coordinated to a nitrogen atom in the aromatic nitrogen-containing base and stacking, to produce a conductive metal-containing nucleic acid duplex. In accordance with these variations in the structure of the molecules of the invention, alternative divalent metal ions may be utilized, again depending upon the ability of such ions to participate with the other substituents of the molecules of the invention in the formation of a conductive metal-containing nucleic acid duplex. The present application sets out assays for the creation of such a duplex, so that others may routinely identify functional substitutions and variations in the structure of the molecules of the invention. Accordingly, although various embodiments of the invention are exemplified herein, other adaptations and modifications may be made within the scope of the invention. The following examples are merely illustrative of alternative embodiments of the invention and are not comprehensive nor limiting in their scope.

EXAMPLE 1

Conductance of MC-CNA

Figure 3A:
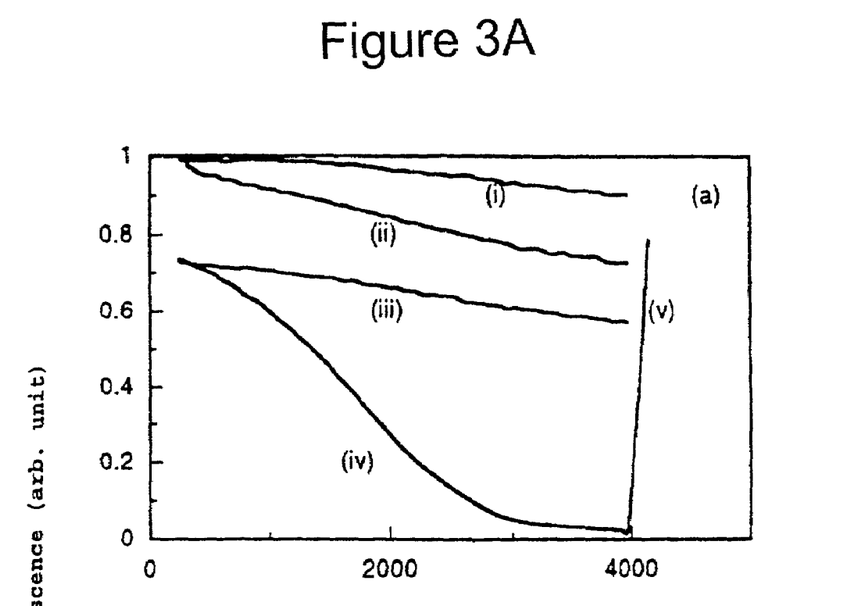
FIGS. 3A and 3B show the fluorescence of fluorescein-labelled oligonucleotides during the formation of M-DNA (see Table 1 for the sequences of the 20-mer and 54-mer) (A) Effect of $Zn^{2+}$ on the 20-mer duplex. (i) Fl-20-mer duplex without $Zn^{2+}$; (ii) Fl-20mer duplex with $Zn^{2+}$; (iii) Fl-20-mer-Rh duplex in the absence of $Zn^{2+}$; (iv) Fl-20mer-Rh duplex in the presence of $Zn^{2+}$; (v) addition of EDTA after the formation of M-DNA. (B) Effect of $Zn^{2+}$ on the 54-mer duplex. (i) Fl-54-mer-Rh with D-site binding protein (1 ug/ml) (the site is located at the centre of the 54-mer duplex) in the presence of $Zn^{2+}$; (ii) addition of proteinase K (50 ug/ml) after 3,000 seconds; (iii) Fl-54mer-Rh duplex wit $Zn^{2+}$. The experiments were performed in 20 mM $NaBO_3$ buffer, pH 9.0 at 20° C. with 10 mM NaCl and 1 mM $Zn^{2+}$ as appropriate. Fluorescence intensities are normalized with respect to the fluorescence intensity of the Fl-20-mer-duplex either in the absence or presence of $Zn^{2+}$.

The conductance of metal-containing nucleic acid duplexes was investigated by preparing duplexes of 20 base pairs of DNA with fluorescein (the electron donor) and rhodamine (the electron acceptor) at opposite ends of the duplex. Methods for such attachment are disclosed in Kessler, 1995, and Haugland, referenced below. Fluorescein and rhodamine fluoresce at different wavelengths, so that it is possible to distinguish fluorescence of the electron donor from fluorescence of the electron acceptor. Under conditions which favour B-DNA (pH less than about 8.0 in the presence of EDTA) the fluorescence of the fluorescein electron donor is partially quenched and the fluorescence of the rhodamine electron acceptor is partially enhanced. This appears to be an example of through space energy transfer (Forster resonance energy transfer or FRET) which has been well-documented in a number of different laboratories (Cheung, H. C. 1991 and Clegg, R. M., 1992). FRET quenching is understood to be due to dipole-dipole interactions along a molecule (not electron conductance) and is highly distance dependent (the effect decreasing with interatom distance in sixth order relationship: $1/r^6$); the value of 25% quenching measured for the 20 base pair duplex is in accordance with the expected FRET behaviour for this length of helix (Clegg, 1992). As shown in FIG. 3a, the fluorescence intensity is relatively stable at pH 9 although at long times there is some loss due to photobleaching.

On addition of $Zn^{2+}$ (1 mM) to the DNA (pH 9), the fluorescence is quenched up to 95% over a period of 1 hr. This rate of increasing quenching mirrors the known rate of formation of M-DNA under these conditions (Lee et al., 1993). Upon reformation of B-DNA by addition of an excess of EDTA (2 mM) after 4,000 sec., the quenching is rapidly reversed. These results are summarized in Table 1.

As a control, the 20-mer duplex (without metal ions) with a fluorescein label shows only a small decrease in intensity due to photobleaching, similar to the effect noted above with respect to ordinary B-DNA (FIG. 3A). Similarly a mixture of two duplexes, one labelled with fluorescein and the other labelled with rhodamine, show minimal quenching either as B-DNA or M-DNA (see Table 1).

To measure the fluorescence life time of the fluorescein when it is attached to the 20-mer oligonucleotide having fluorescein at one end and rhodamine at the other end, the fluorescein is irradiated with a picosecond pulse of laser light and the fluorescence decay of the excited fluorescein is then followed for several nanoseconds. Normally (as is the case with B-DNA) the t½ for decay is about 3 nanoseconds. Upon conversion to the $Zn^{2+}$ form of M-DNA as described above, the t½ drops to about 0.3 nanoseconds. This extremely fast decay is consistent with electron conductivity by the M-DNA helix.

Figure 3B:
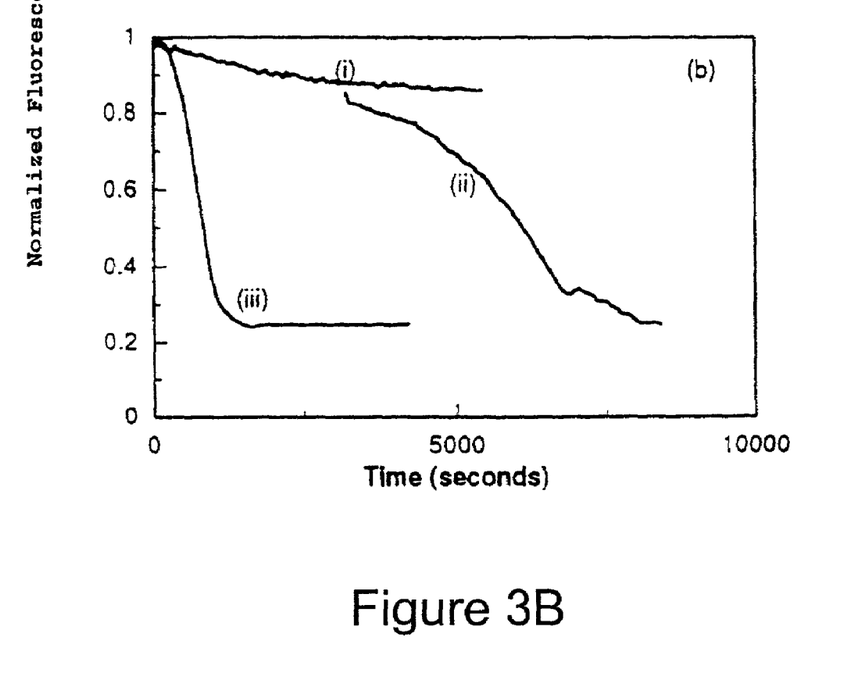

Electron transfer in the $Zn^{2+}$ isomer of M-DNA was investigated in a longer helix of 54 base pairs (this 54mer has an estimated length of over 150 Å). This 54mer also contained the recognition site for the D-site binding protein (Roesler et al., 1992) in the middle of the sequence. As shown in FIG. 3B, there is no quenching in the absence of metal ions in the 54mer, this may be because the fluorophores are well separated so that there is no FRET. However, upon addition of $Zn^{2+}$ under appropriate conditions to form M-DNA (1 mM $Zn^{2+}$, pH 9), the fluorescent intensity rapidly drops to 25% of the initial value, demonstrating efficient conductance over the length of the 54mer.

In the presence of the D-site binding protein, under conditions appropriate to form M-DNA, the fluorescence intensity of the 54mer only drops slowly. However, as judged from the ethidium fluorescence assay (Lee et al., 1993), the majority of the 54mer DNA is in the form of M-DNA (which does not bind ethidium). This demonstrates that the D-site DNA-binding protein is interrupting the flow of electrons along the 54mer M-DNA duplex. As a control, the D-site binding protein has no effect on the quenching of the 20-mer (which has no D-site binding sequence, see Table 1). On addition of protease at 3000 seconds to the D-site binding protein:54mer M-DNA complex, the protein is cleaved and the fluorescence intensity begins to drop, eventually reaching the minimum value of 25% of the initial fluorescence value. This experiment is a simple example of a bioreactive electronic switch comprising conductive metal-containing nucleic acid and a DNA-binding protein capable of disrupting the conductive duplex. Such a switch is also analogous to an electronic memory element, having two interchangeable states, conductive and non-conductive.

TABLE 1

Normalized Fluorescence of the Fluorescein-labelled oligonucleotides

| Oligonucleotide | Treatment | Fluorescence |
|---|---|---|
| Fl-20-mer duplex | none | 1 |
| Fl-20-mer duplex | +$Zn^{2+}$ | 0.98 |
| Fl-20-mer duplex | +$Zn^{2+}$ at pH 8.0 | 0.92 |
| Fl-20-mer single strand | none | 0.87 |
| Fl-20-mer duplex + Rh-20-mer duplex | none | 0.97 |
| Fl-20-mer-Rh duplex | none | 0.73 |
| Fl-20-mer-Rh duplex | +$Zn^{2+}$ | 0.05 |
| Fl-20-mer-Rh duplex | +$Zn^{2+}$ + EDTA | 0.87 |
| Fl-20-mer-Rh duplex | +$Zn^{2+}$ at pH 8.0 | 0.92 |
| Fl-20-mer-Rh duplex | +$Co^{2+}$ | 0.05 |
| Fl-20-mer-Rh duplex | +$Co^{2+}$ + EDTA | 0.7 |
| Fl-20-mer-Rh duplex | +$Ni^{2+}$ | 0.06 |
| Fl-20-mer-Rh duplex | +$Ni^{2+}$ +EDTA | 0.7 |
| Fl-20-mer-Rh duplex | +$Mg2+$ | 0.83 |
| Fl-20-mer-Rh duplex | +D-site binding protein + $Zn^{2+}$ | 0.06 |
| Fl-54-mer-Rh | +D-site binding protein + $Zn^{2+}$ | 1 |
| Fl-54-mer-Rh | +$Zn^{2+}$ | 0.21 |

Conversion to M-DNA was performed in 20 mM $NaBO_3$ buffer, pH 9.0. Fluorescence assays were carried out in 20 mM Tris pH 8.0. Other conditions were as follows: 10 mM NaCl at 20 EC and 1 mM $Zn^{2+}$ or 0.2 mM $Co^{2+}$ or 0.2 mM $Ni^{2+}$ or 2 mM EDTA as appropriate. Excitation was at 490 nm with emission measured at 520 nm. Fluorescence intensities are normalized with respect to the fluorescence intensity of the Fl-20-mer-duplex either in the absence or presence of $Zn^{2+}$ and were measured after 3,000 sec.

Sequences and nomenclature: The oligonucleotides were labelled 5' with fluorescein (Fl) or rhodamine (Rh) using standard attachment methods and constructs, for example as used in DNA sequencing. The fluorescein 20-mer was as follows: (SEQ ID NO: 1): Fl-5'-d(GTC ACG ATG GCC CAG TAG TT). The rhodamine 20-mer was as follows: (SEQ ID NO: 2): Rh-5'-d(AAC TAC TGG GCC ATC GTG AC). The same unlabelled sequence was used to produce the Fl-20-mer-duplex. The Fl-54-mer was as follows: (SEQ ID NO: 3): Fl-5'-d(GCT ATG ATC CAA AGG CCG GCC CCT TAC GTC AGA GGC GAG CCT CCA GGT CCA GCT) (The D-site is underlined). The Rh-54mer was as follows: (SEQ ID NO: 4): Rh-5'-d(AGC TGG ACC TGG AGG CTC GCC TCT GAC GTA AGG GGC CGG CCT TTG GAT CAT AGC). The same unlabelled sequence was used to produce the Fl-54-mer duplex.

This Example demonstrates a method for converting a nucleic acid duplex to a conductive metal-containing nucleic acid duplex, in this case M-DNA. The excited electron on the fluorescein is rapidly transmitted down the M-DNA helix to the rhodamine; demonstrating rapid and efficient electron transfer along the M-DNA. The $Co^{2+}$ and $Ni^{2+}$ isomers of M-DNA show quenching of the fluorescein by up to 95% even in the absence of the rhodamine acceptor (Table 1). This indicates that the M-DNA can itself act as an electron acceptor.

EXAMPLE 2

Physical Properties of M-DNA

Figure 1:
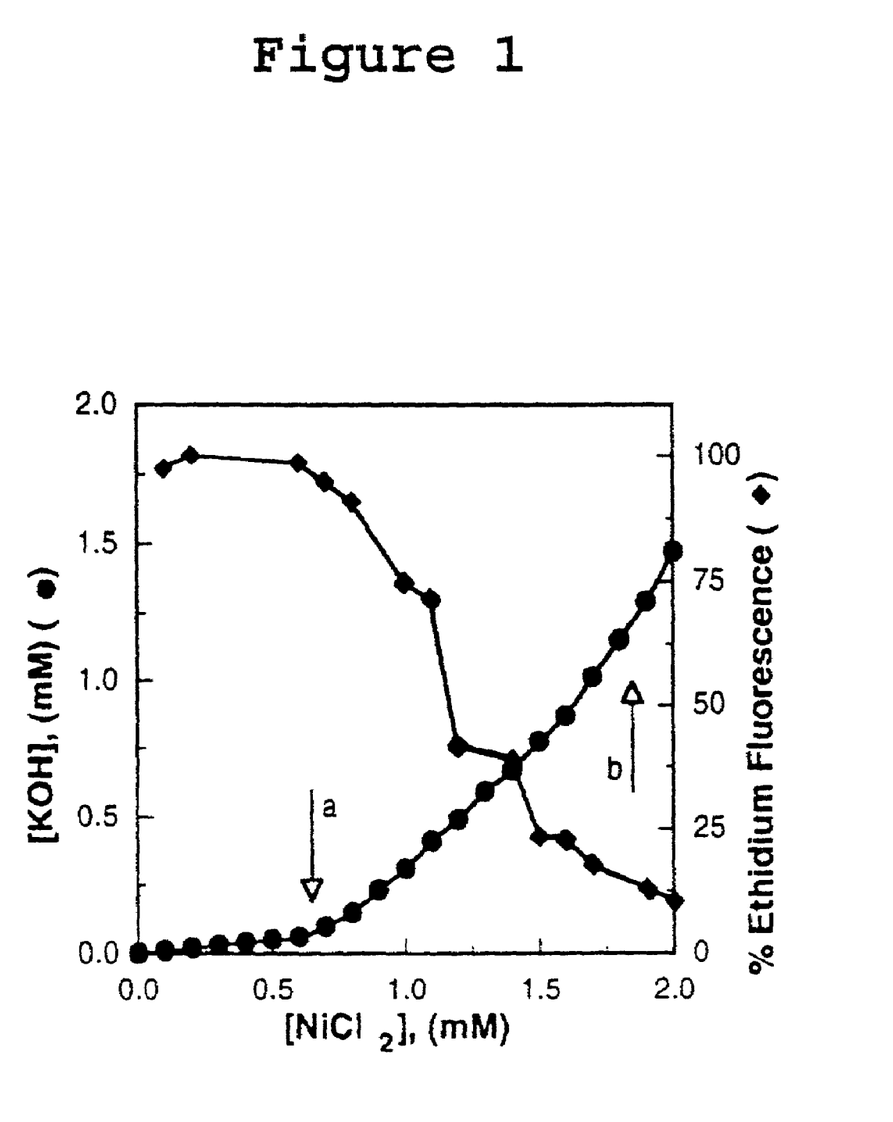

The mobility of linear or covalently closed circular forms of M-DNA in agarose gels is only slightly less than that of B-DNA (indicating that treatment in accordance with the invention to produce M-DNA need not cause condensation or aggregation of the DNA). NMR studies show that the imino protons of T (pKa 9.9) and G (pKa 9.4) may not be present in M-DNA, illustrating that the imine protons may be replaced by the divalent metal cation in M-DNA. The release of protons during the formation of M-DNA may be indicative of this phenomenon. As shown in FIG. 1, M-DNA begins to form at about 0.7 mM $NiCl_2$ (as judged from the ethidium fluorescence assay); there is a concomitant release of protons so that KOH may be added to maintain the pH at 8.5. At 1.8 mM $NiCl_2$, M-DNA formation is virtually complete and the complex starts to precipitate. This suggests that one proton is released per $Ni^{2+}$ atom per base pair during the formation of M-DNA. The $Zn^{2+}$ and $Co^{2+}$ isomers of M-DNA also release protons during formation, and precipitation of the complex may occur at a lower concentration of divalent metal ion than with $Ni^{2+}$. These results are consistent with the metal ion being coordinated to the N3 position of T and N1 of G in the base pairs.

Figure 2A:
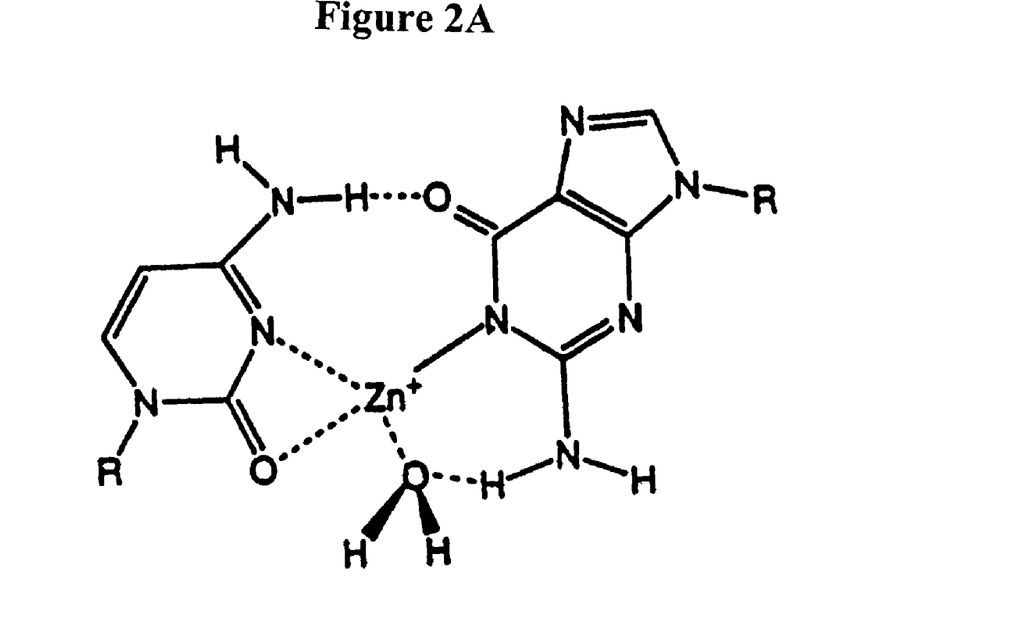
FIGS. 2A and 2B show a putative structure of M-DNA, FIG. 2A showing G-C and FIG. 2B showing A-T base pairs. Putative hydrogen bonds and interactions between $Zn^{2+}$ and its coordinating groups are shown as dotted lines.
Figure 2B:
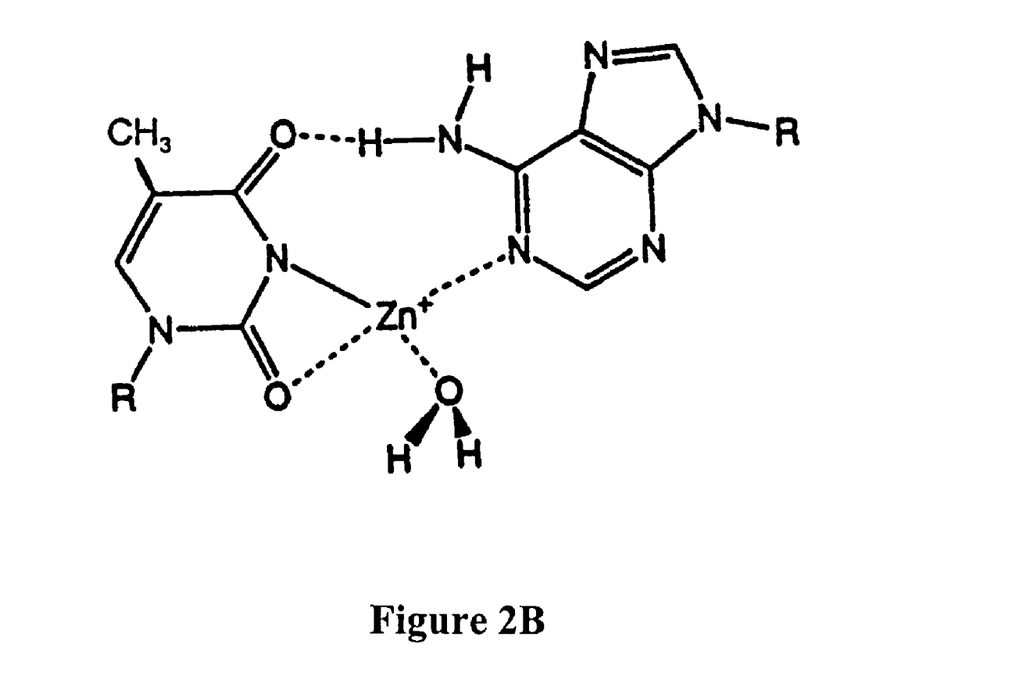

Based on these observations, a putative structure for M-DNA can be modelled as shown in FIG. 2. This model reflects experimental results relating to one aspect of the present invention, and does not limit the invention to any such putative structure. The model may nevertheless be helpful to others in practising routine variations of the invention. In this putative structure, the A-T and G-C base pairs are isomorphous, which is a common feature of stable helical nucleic acid structures (Palecek, 1991). Compared to a Watson-Crick base pair, insertion of the metal ion with an imino N-metal bond of 2 Å (Swaminathan and Sundralingham, 1979; DeMeester, 1973; McGall and Taylor, 1973) requires a 20°–30° rotation of the bases which opens up the minor groove. One hydrogen bond is retained in both base pairs, which may facilitate rapid reformation of normal B-DNA without denaturation of the helix on removal of the metal ion. The coordination geometry of the metal ion may be distorted square planar with the solvent providing the fourth ligand in some embodiments. The UV-Vis spectrum of the $Co^{2+}$ and $Ni^{2+}$ isomers of M-DNA have peaks in the visible with $\epsilon$ of 20 and 60 mol-1 cm-1 respectively; an observation which is consistent with this geometry (Lever, 1988). In this putative model of an M-DNA duplex, the metal ion is buried within the helix and d-$\pi$ bonding may occur with the aromatic bases above and below the metal ion. The putative model helix could be considered as a distorted member of the B-type helix family in agreement with the unremarkable CD spectrum (Lee et al, 1993.). On average the model metal-metal distance is 4 Å.

EXAMPLE 3

M-DNA Is Nuclease Resistant

Figure 4:
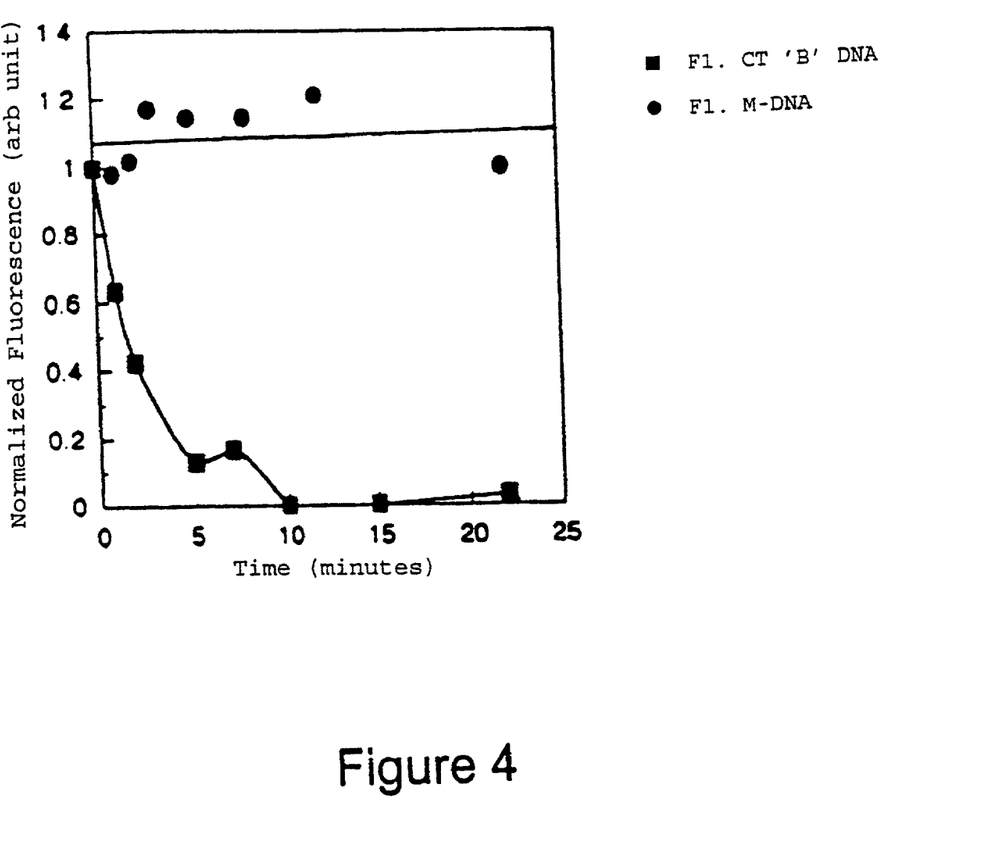

The nuclease resistance of M-DNA was established by assaying the amount of duplex M-DNA remaining as a function of time in the presence of DNase I, as shown in FIG. 4. The amount of DNA was assessed by the ethidium fluorescence assay (under conditions where M-DNA rapidly reverts to B-DNA, i.e. pH 8 in the presence of EDTA, so that ethidium can bind the DNA for the purpose of the assay). The digestion was performed at 37° C. in 10 mM Tris-HCl, pH 7.4, 5 mM $MgCl_2$, 1 mM $NiCl_2$, 1 mg/ml gelatin, and 0.2 µg/ml DNase I. The $Ni^{2+}$ form of M-DNA was preformed for the assay at pH 9, before adding it to the digestion buffer; B-DNA was added directly to the digestion buffer. The graph shows that the M-DNA is resistant to nuclease digestion while B-DNA is digested in about 10 minutes. The results also demonstrate that the $Ni^2l$ form of M-DNA is stable at physiological pH, a characteristic which may facilitate the use of Ni-M-DNA to mediate physiological responses in vivo, such as DNA immunization (in which the DNA vaccine expresses an antigenic protein) or antisense applications (in which injected M-DNA inhibits the expression of a gene).

EXAMPLE 4

M-DNA is Immunogenic

B-DNA is generally not immunogenic. However, synthetic or modified nucleic acids that are nuclease resistant may be capable of producing an antibody response under certain conditions (Braun and Lee, 1988).

To test the immunogenicity of M-DNA, Balb/C mice were immunized interperitoneally three times at ten day intervals with 10 µg of nickel-containing M-DNA, with and without methylated bovine serum albumin (Me-BSA). The first injection was with complete Freunds adjuvant and subsequent injections were with incomplete Freunds adjuvant. Three days after the final injection, blood was obtained by tail bleeding and the serum was tested for the present of antiM-DNA antibodies using nickel M-DNA coated polyvinylchloride plates in a SPIRA assay, using methods known in the art (Braun and Lee, 1988).

Figure 5:
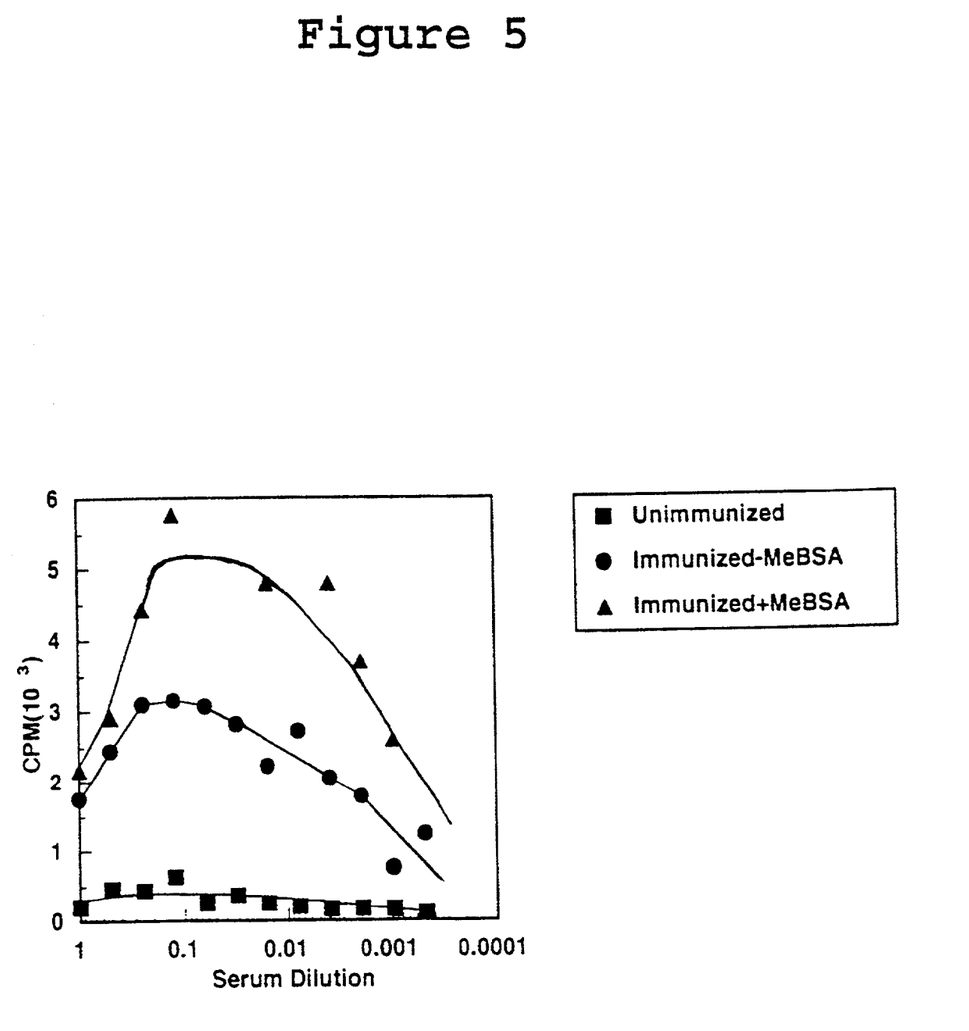

The results, shown in FIG. 5, demonstrate that the mice immunized with M-DNA (with and without Me-BSA) show antibody titres to M-DNA up to about 1:1000 dilution. The control sera from an unimmunized mouse contains no antibodies to M-DNA. The ability of M-DNA to elicit an immune response is consistent with the finding that M-DNA may be nuclease resistant (see Braun and Lee, 1988). Accordingly, in some embodiments, M-DNA may be useful for immunizing a host, for example in methods as disclosed in U.S. Pat. Nos. 5,679,647; 5,804,566 or U.S. Pat. No. 5,830,877 issued to Carson et al. on, respectively 21 Oct. 1997, 8 Sep. 1998 and 3 Nov. 1998 (and incorporated herein by reference).

All publications and patents mentioned in this specification are indicative of the level of skill of those skilled in the art to which this invention pertains. All publications and patents are herein incorporated by reference to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

REFERENCES

The following documents are incorporated herein by reference.

1. Dandliker, P. J., Holmlin, R. E. & Barton, J. K., *Science*, 275:1465–1468 (1997).
2. Hall, D. B., Holmlin, R. E. & Barton, J. K., *Nature*, 382:731–735 (1996).
3. Arkin, M. R., Stemp, E. D. A., Holmlin, R. E., Barton, J. K., Hormann, A., Olson, E. J. C. & Barbara, P. F., *Science*, 273:475–479 (1996).
4. Murphy, C. J., Arkin, M. R., Jenkins, Y., Ghatlia, N. D., Bossmann, S. H., Turro, N. J. & Barton, J. K., *Science*, 262:1025–1029 (1993).
5. Lewis, F. D., Wu, T., Zhang, Y., Letsinger, R. L., Greenfield, S. R., & Wasielewski, M. R., *Science*, 277:673–676 (1997).
6. Taubes, G., *Science*, 275:1420–1421 (1997).
7. Lee, J. S., Latimer, L. J. P. & Reid, R. S., *Biochem. Cell Biol.*, 71:162–168 (1993).
8. Palecek, E., *CRC Crit. Rev. Biochem. Mol. Biol.*, 26:151–226 (1991).
9. Yagil, G., *CRC Crit. Rev. Biochem. Mol. Biol.*, 26: 475–559 (1991).
10. Swaminathan, V. & Sundralingham, M., *CRC Crit. Rev. Biochem. Mol. Biol.*, 14: 245–336 (1979).
11. DeMeester, P., Goodgame, D. M. L., Skapski, A. C. & Warnke, Z., *Biochem. Biophys. Acta*, 324:301–303 (1973).
12. McGall, M. J. & Taylor, M. R., *Biochem. Biophys. Acta*, 390:137–139 (1973).
13. Lever, A. B. P. "*Inorganic Electronic Spectroscopy*" (Elsevier, Amsterdam) (1988).
14. Cheung, H. C. in "*Topics in Fluorescence Spectroscopy*" pp. 128–171, Ed. Lakowicz, J. R. (Plenum, New York) (1991).
15. Clegg, R. M. *Methods in Enzymology*, 211:353–371 (1992).
16. Roesler, W. J., McFie, P. J. & Dauvin, C., *J. Biol. Chem.*, 267: 21235–21243 (1992).
17. Lilley, D. M. J. & Clegg, R. M., *Ann. Rev. Biophys. Biomol. Str.* 22: 299–328 (1993).
18. Seeman, N. C. & Kallenbach, N. R., *Ann. Rev. Biophys. Biomol. Str.*, 23:53–86 (1994).
19. Brunger, A. 1. X-PLOR Manual, ver. 3.1 (University Press New Haven USA (1993).
20. Braun, R. P. and Lee, J. S., *J. Immunol.*, 141: 2084–2089 (1988).
21. Kessler, C. in *Nonisotopic Probing, Blotting and Sequencing*, L. J. Kricka, Ed., Academic Press (1995) pp. 3–40.
22. Haugland, R. P. *Handbook of Fluorescent Probes and Reserch Chemicals*, 6th Ed., p. 157.
23. Marmur, J. & Doty, P., *J. Mol. Biol*, 5:109–118 (1962).

What is claimed is:

1. A method of eliciting an immune response to an antigen comprising administering to the animal a metal-containing nucleic acid duplex encoding the antigen, wherein the metal-containing nucleic acid duplex comprises a first strand of nucleic acid and a second strand of nucleic acid, the first and the second nucleic acid strands each comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases on the first and the second nucleic acid strands forming hydrogen-bonded base pairs in stacked arrangement along the length of the metal-containing nucleic acid duplex, at least some of the hydrogen-bonded base pairs comprising an interchelated divalent metal cation coordinated to a nitrogen atom in one of the aromatic nitrogen-containing aromatic bases, wherein the immune response elicited in the animal to the antigen encoded by the metal-containing nucleic acid is an antibody response.

2. The method of claim 1 wherein the first and the second nucleic acid strands are deoxyribonucleic acid and the nitrogen-containing aromatic bases are selected from the group consisting of adenine, thymine, guanine and cytosine.

3. The method of claim 1 wherein the divalent metal cation is selected from the group consisting of $Zn^{2+}$, $Co^{2+}$, and $Ni^{2+}$.

4. The method of claim 1 wherein the divalent metal cations are substituted for imine protons of the nitrogen-containing aromatic bases, and the nitrogen-containing aromatic bases are selected from the group consisting of thymine and guanosine.

5. The method of claim 1 wherein at least one of the aromatic nitrogen-containing aromatic bases is thymine, having an N3 nitrogen atom, and the divalent metal cation is coordinated by the N3 nitrogen atom.

6. The method of claim 1 wherein at least one of the aromatic nitrogen-containing aromatic bases is guanine, having an N1 nitrogen atom, and the divalent metal cation is coordinated by the N1 nitrogen atom.

7. The method of claim 1, wherein the metal-containing nucleic acid further comprises an electron source electrically coupled to the metal-containing nucleic acid duplex.

8. The method of claim 7, wherein the metal-containing nucleic acid further comprises an electron sink electrically coupled to the metal-containing nucleic acid duplex.

9. The method of claim 1, wherein the animal is a human.

10. A method of eliciting an immune response to an antigen comprising administering to the animal an adjuvant and a metal-containing nucleic acid duplex encoding the antigen, wherein the immune response elicited in the animal to the antigen encoded by the metal-containing nucleic acid is an antibody response, and wherein the metal-containing nucleic acid duplex is made by the process comprising:
 a) providing a nucleic acid duplex comprising a first strand of nucleic acid and a second strand of nucleic acid, the first and the second nucleic acid strands comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases on the first and the second nucleic acid strands forming hydrogen-bonded base pairs in stacked arrangement along the length of the nucleic acid duplex; and,
 b) subjecting the nucleic acid duplex to a basic solution in the presence of a divalent metal cation under conditions effective to form a conductive metal-containing nucleic acid duplex, wherein at least some of the hydrogen-bonded base pairs of the conductive metal-containing nucleic acid duplex comprise interchelated divalent metal cation coordinated to a nitrogen atom in one of the aromatic nitrogen-containing aromatic bases.

11. The method of claim 10 wherein the first and the second nucleic acid strands are deoxyribonucleic acid and the nitrogen-containing aromatic bases are selected from the group consisting of adenine, thymine, guanine and cytosine.

12. The method of claim 10 wherein the divalent metal cation is selected from the group consisting of $Zn^{2+}$, $Co^{2+}$, and $Ni^{2+}$.

13. The method of claim 10 wherein the divalent metal cations are substituted for imine protons of the nitrogen-containing aromatic bases, and the nitrogen-containing aromatic bases are selected from the group consisting of thymine and guanosine.

14. The method of claim 10 wherein at least one of the aromatic nitrogen-containing aromatic bases is thymine, having an N3 nitrogen atom, and the divalent metal cation is coordinated by the N3 nitrogen atom.

15. The method of claim 10 wherein at least one of the aromatic nitrogen-containing aromatic bases is guanine, having an N1 nitrogen atom, and the divalent metal cation is coordinated by the N1 nitrogen atom.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide sequences.

<400> SEQUENCE: 1
gtcacgatgg cccagtagtt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide sequences.

<400> SEQUENCE: 2
aactacttgg ccatcgtgac                                              20

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide sequences.

<400> SEQUENCE: 3
gctatgatcc aaaggccggc cccttacgtc agaggcgagc ctccaggtcc agct        54

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide sequences.

<400> SEQUENCE: 4
agctggacct ggaggctcgc ctctgacgta agggccggc ctttggatca tagc         54
```